(12) United States Patent
Dodick (10) Patent No.: US 7,736,329 B2
(45) Date of Patent: Jun. 15, 2010

(54) SURGICAL INSTRUMENT WITH A SLEEVE FOR USE DURING EYE SURGERY

(76) Inventor: Jack M. Dodick, 535 Park Ave., New York, NY (US) 10021

( * ) Notice: Subject to any disclaimer, the term of this patent is extended or adjusted under 35 U.S.C. 154(b) by 354 days.

(21) Appl. No.: 11/558,318

(22) Filed: Nov. 9, 2006

(65) Prior Publication Data

US 2007/0106303 A1 May 10, 2007

Related U.S. Application Data (63) Continuation-in-part of application No. 11/479,964, filed on Jun. 30, 2006.

(60) Provisional application No. 60/697,824, filed on Jul. 7, 2005, provisional application No. 60/731,001, filed on Oct. 28, 2005.

(51) Int. Cl.
  *A61M 3/00* (2006.01)

(52) U.S. Cl. ............ 604/43; 604/163; 604/171; 604/198; 604/204; 604/175; 604/39; 604/22; 604/264; 604/27; 604/40; 604/902; 606/169

(58) Field of Classification Search .......... 604/22, 604/169, 175, 902, 163, 171, 198, 204, 264, 604/27, 39, 40, 43; 606/169
See application file for complete search history.

(56) References Cited

U.S. PATENT DOCUMENTS

| | | | |
|---|---|---|---|
| 3,589,363 A | | 6/1971 | Banko et al. |
| 3,659,607 A | | 5/1972 | Banko |
| 3,888,249 A | * | 6/1975 | Spencer ............ 604/247 |
| 4,431,030 A | * | 2/1984 | Nachazel ............ 138/45 |
| 4,515,583 A | | 5/1985 | Sorich |
| 4,648,871 A | * | 3/1987 | Jacob ............ 604/45 |
| 5,084,009 A | | 1/1992 | Mackool |
| 5,217,001 A | * | 6/1993 | Nakao et al. ............ 600/123 |
| 5,324,282 A | | 6/1994 | Dodick |
| 5,634,912 A | * | 6/1997 | Injev ............ 604/264 |
| 5,674,240 A | * | 10/1997 | Bonutti et al. ............ 606/198 |
| 5,685,841 A | * | 11/1997 | Mackool ............ 604/22 |
| 5,795,323 A | * | 8/1998 | Cucin ............ 604/22 |
| 5,800,414 A | * | 9/1998 | Cazal ............ 604/523 |
| 5,873,851 A | * | 2/1999 | Nilsson ............ 604/43 |
| 5,879,356 A | * | 3/1999 | Geuder ............ 606/107 |
| 5,906,611 A | | 5/1999 | Dodick et al. |
| 5,919,157 A | | 7/1999 | Strukel |
| 6,132,436 A | * | 10/2000 | Portney ............ 606/107 |

(Continued)

*Primary Examiner*—Nicholas D Lucchesi
*Assistant Examiner*—Scott Medway
(74) *Attorney, Agent, or Firm*—Leason Ellis LLP (57) ABSTRACT

According to one exemplary embodiment, a surgical instrument for insertion in an incision during surgical treatment and removal of tissue includes an inner elongated needle having an ovoid shape and a bore extending therethrough; and a hollow sleeve that surrounds the ovoid shaped needle such that two side regions of the needle contact an inner surface of the sleeve at two locations so as to define a pair of fluid channels that are located between convex outer surfaces of the needle and the inner surface of the sleeve. The shape of the sleeve, when deformed by insertion of the needle, is configured to be received within the incision during the surgical treatment and removal of the tissue so as to plug opposite ends of the incision and provide an at least substantially closed surgical site.

17 Claims, 10 Drawing Sheets

U.S. PATENT DOCUMENTS

| | | | |
|---|---|---|---|
| 6,361,520 B1 * | 3/2002 | Rockley | 604/22 |
| 6,592,544 B1 * | 7/2003 | Mooney et al. | 604/43 |
| 6,669,708 B1 * | 12/2003 | Nissenbaum et al. | 606/153 |
| 6,689,107 B1 * | 2/2004 | Choudhary | 604/192 |
| 6,790,120 B1 * | 9/2004 | Murray | 446/220 |
| 6,827,710 B1 * | 12/2004 | Mooney et al. | 604/500 |
| 2003/0144674 A1 * | 7/2003 | Loubens et al. | 606/148 |
| 2006/0036215 A1 * | 2/2006 | Boukhny | 604/175 |

* cited by examiner

SURGICAL INSTRUMENT WITH A SLEEVE FOR USE DURING EYE SURGERY

CROSS REFERENCE TO RELATED APPLICATIONS

The present application is a continuation-in-part of patent application Ser. No. 11/479,964, filed on Jun. 30, 2006, which claims the benefit of U.S. patent application No. 60/697,824, filed Jul. 7, 2005, and No. 60/731,001, filed Oct. 28, 2005, all of which are expressly hereby incorporated by reference in their entireties.

TECHNICAL FIELD

The present invention relates to a surgical instrument, and more particularly, relates to a surgical instrument that operates on tissue and includes a feature that substantially seals an incision through which the instrument is inserted to contact the tissue, thereby creating a closed operation system.

BACKGROUND

In a number of different surgical operations, the objective is to locate, break apart and remove unwanted tissue from the body. For example, one of the more common aliments associated with the eye is the formation and presence of cataracts in the eye. As is known, a cataract is a cloudy area in the eye's lens that can cause vision problems. The lens is the part of the eye that helps focus light onto the retina. The lens is made mostly of water and protein. The protein is arranged to let light pass through and focus on the retina. Sometimes some of the protein clumps together and starts to cloud a small area of the lens. This is a cataract. The most common type of cataract is related to aging.

There are a number of different surgical techniques for breaking apart and removing a cataract from the eye and as a result, there are a number of different surgical instruments that can be used to accomplish this task. However, each of these surgical instruments, either alone or in combination with other instruments, is constructed to accomplish the same objective, namely breaking apart the cataract and then removing the tissue from the eye.

Figure 1:
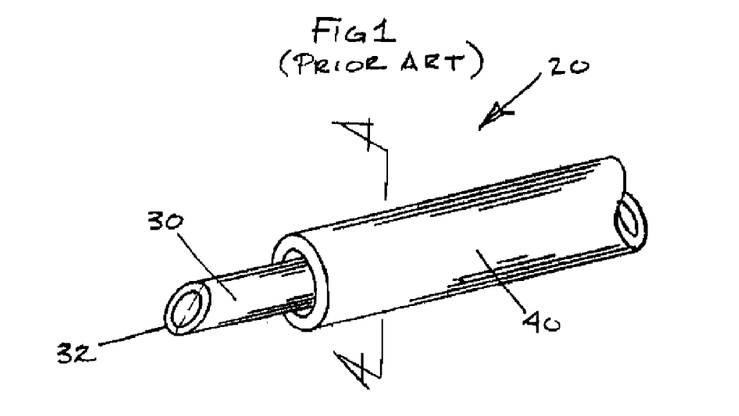
FIG. 1 is a perspective view of a conventional bimanual surgical instrument.
Figure 2:
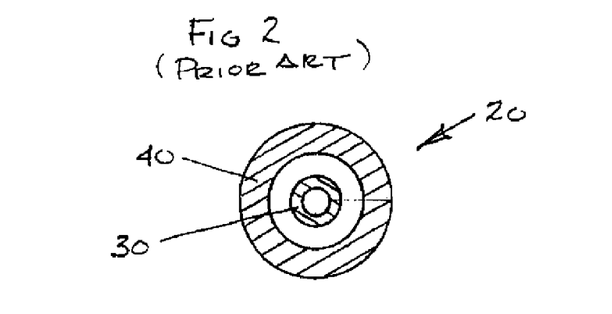
FIG. 2 is a cross-sectional view taken along line 2-2 of FIG. 1.
Figure 3:
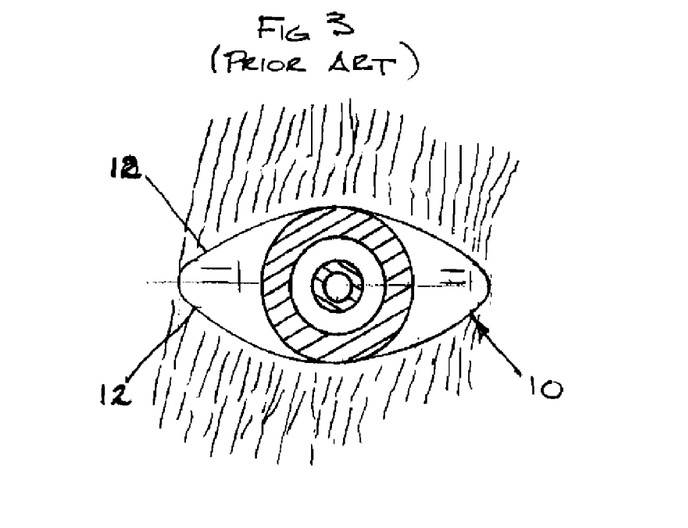
FIG. 3 is a cross-sectional view taken along line 2-2 of FIG. 1 after the surgical instrument has been inserted into a wound.

Small incision cataract surgery is today one of the more prevalent operations for removing a cataract from the eye and in particular, the small incision cataract surgery is most commonly performed by ultrasound phacoemulsification. With reference to FIGS. 1-3, a coaxial surgical instrument 20 defined by an ultrasonic probe 30 with coaxial infusion provided by a sleeve 40 of the probe 30 is typically inserted through a wound or incision 10 made in the cornea, limbus or sclera of the eye. The incision 10 is usually between about 2.2 mm to 3.5 mm but it may be slightly smaller or larger depending on the particular application and patient. The infusion maintains the anterior chamber while the lens nucleus is emulsified due to longitudinal ultrasonic vibrations provided at the working tip of the probe 30. The infusion (treatment fluid) baths the tissue in the region adjacent a working tip 32 and the probe 30 includes means adjacent the working tip 32 for withdrawing the suspension of particles of the tissue in the fluid (infusion) resulting from the ultrasonic vibration of the working tip 32. This type of instrument 20 is described in more detail in U.S. Pat. No. 3,589,363, which is hereby incorporated by reference in its entirety. Following emulsification and aspiration of the nucleus, the softer cortex of the lens can be removed by a different co-axial instrument through the same incision. This other co-axial instrument usually has a smaller diameter than the ultrasonic probe 30. Alternatively, the softer cortex can be removed in a bimanual fashion through two paracentesis incisions in the cornea or limbus of the eye, which are separate incisions than the emulsification incision and much smaller in length, e.g., usually 1 mm or less.

More recently, another type of emulsification has become popular. More specifically, bimanual ultrasound emulsification has become popular in which the infusion (treatment fluid) and emulsification are divorced and delivered through two separate incisions which can each range in length between about 1 mm and 2.5 mm. The advantage of the bimanual approach is that the final incision size is smaller than the size of the single incision that is used in the above co-axial approach. This leads to quicker healing of the incision (wound) and quicker rehabilitation of the patient.

Energy sources other than ultrasound have been used to emulsify the lens in both the coaxial and manual approaches. For example, the energy source of the probe can be laser energy as described in greater detail in U.S. Pat. Nos. 5,324,282 and 5,906,611, both of which are hereby incorporated by reference in their entireties and which the present applicant is a named inventor. Other energy sources, such as water or water jets can be used to emulsify or break up the lens.

In all approaches, whether coaxial or bimanual, the cannulas that define the surgical instrument, such as instrument 20, are usually round and are inserted through a slit incision or wound 10. This creates a situation where it is not possible to obtain a closed system since edges 12 of the incision 10 separate due to the presence of the cannulas 30, 40, thereby creating two pockets or openings 11 at the ends of the incision 10 where the cannulas 30, 40 are not present as shown in FIG. 3. As a result, fluid leakage occurs on either side of the cannulas, i.e., the two end pockets or openings 11. A true closed system is advisable so that no wound leakage occurs. This would provide the surgeon with a more stable anterior chamber leading to greater intraoperative control in which the anterior chamber would not fluctuate between deep and shallow, which can lead to damage of intraocular structures within the eye during emulsification, including the cornea, iris, and posterior lens capsule of the eye.

SUMMARY

According to one exemplary embodiment, a surgical instrument for insertion in an incision during surgical treatment and removal of tissue includes an inner elongated needle having an ovoid shape and a bore extending therethrough; and a hollow sleeve that surrounds the ovoid shaped needle such that two side regions of the needle contact an inner surface of the sleeve at two locations so as to define a pair of fluid channels that are located between convex outer surfaces of the needle and the inner surface of the sleeve. The shape of the sleeve, when deformed by insertion of the needle, is configured to be received within the incision during the surgical treatment and removal of the tissue so as to plug opposite ends of the incision and provide an at least substantially closed surgical site. In other words, the skin edges that define the incision conform to and contact the perimeter shape of the sleeve such that there are substantially no gaps between the instrument and the skin edges. In this manner, leakage of fluid in the areas around the inserted instrument is substantially eliminated, thereby forming a closed surgical site.

In another embodiment, a surgical instrument for insertion in an incision during surgical treatment and removal of tissue includes an inner elongated needle having an ovoid shape and a bore extending therethrough; and a hollow sleeve that surrounds the ovoid shaped needle such that two side regions of the needle contact an inner surface of the sleeve at two locations so as to define a pair of fluid channels that are located between convex outer surfaces of the needle and the inner surface of the sleeve. In a relaxed condition prior to insertion of the needle, the sleeve has an ovoid shape.

As with the other embodiment, the ovoid shape of the sleeve is configured to be received within the incision during the surgical treatment and removal of the tissue so as to plug opposite ends of the incision and provide an at least substantially closed surgical site.

Further aspects and features of the present invention can be appreciated from the appended Figures and the accompanying written description.

BRIEF DESCRIPTION OF THE DRAWING FIGURES

The foregoing and other features of the present invention will be more readily apparent from the following detailed description and drawings of the illustrative embodiments of the invention wherein like reference numbers refer to similar elements and in which.

DETAILED DESCRIPTION OF PREFERRED EMBODIMENTS

Figure 4:
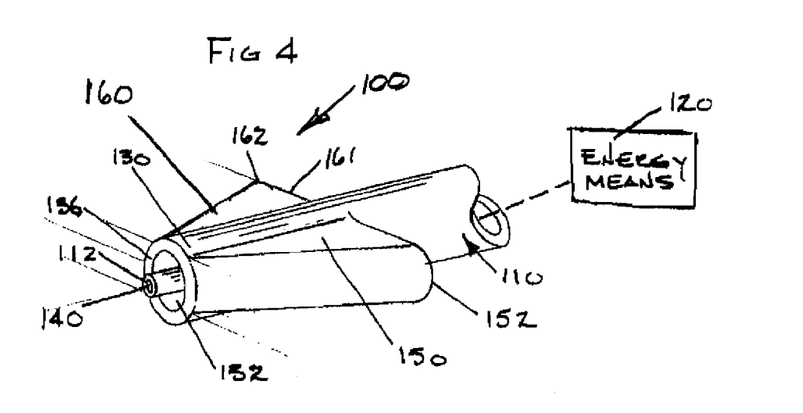
FIG. 4 is a perspective view of a surgical instrument according to a first embodiment of the present invention.
Figure 5:
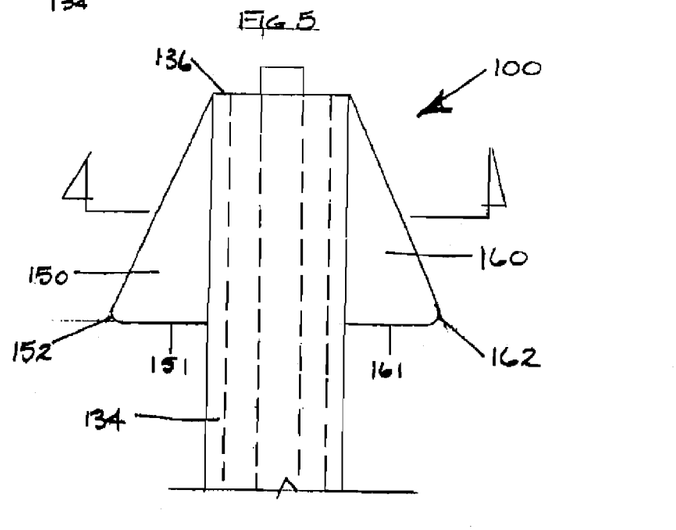
FIG. 5 is a side elevation view of the instrument of FIG. 4.
Figure 6:
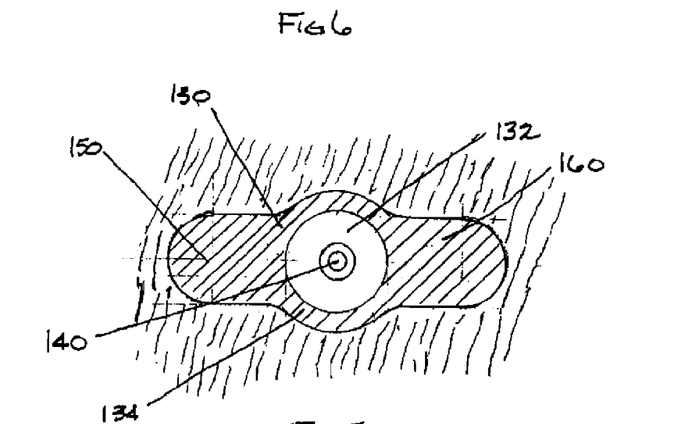
FIG. 6 is a cross-sectional view taken along the line 6-6 of FIG. 5.

The present invention according to one aspect is generally embodied in FIGS. 4-6 in which a surgical instrument 100 according to one exemplary embodiment is illustrated. The surgical instrument 100 is intended to overcome the above-described leakage deficiencies that are associated with conventional coaxial or bimanual cannulas that are inserted into the incision 10 (FIG. 3) and as a result, the surgical instrument 100 includes a feature that seals or plugs the otherwise open ends of the incision that are formed when a conventional instrument is inserted into the incision.

The surgical instrument 100 of FIGS. 4-6 is of the type that is typically used in a coaxial infusion application and therefore, the surgical instrument 100 has an elongated body 110 that terminates in a working tip (distal tip) 112. The elongated body 110 contains an energy means, generally indicated at 120, that is operatively connected to the working tip 112 to permit the working tip 112 to emit energy that is sufficient to break apart and emulsify the lens nucleus when the working tip 112 is placed at the surgical site. For example, the energy means 120 can be an ultrasound source, a laser, or a fluid means, such as pressurized water or water jets. The body 110 typically has a circular shape.

The tip 112 is surrounded by a sleeve 130. A first passage 132 is formed between the body of the tip 112 and the sleeve 130. The first passage 132 is in fluid communication with a means for supplying fluid (treatment fluid/infusion fluid) to the first passage 132. The means can include an inlet to which a treatment fluid supply (not shown) can be coupled. The sleeve 130 also typically has a circular shape and is arranged coaxial with the tip 112.

The tip 112 also includes a second passage 140 that is formed as a part thereof and extends to the distalmost portion of the tip 112. The second passage 140 is fluidly connected to a means for supplying a suction force to the second passage 140. The means can include an outlet to which a suction pump (not shown) can be coupled. In the illustrated embodiment, the first passage 132 is formed radially about the second passage 140.

It will be appreciated that the elongated body 110 can be moved axially within the sleeve 130 and therefore, the distance that the tip 112 protrudes beyond the end of the body 110 can be adjusted. For example, if it is desired to have the tip 112 extend further from the distal end of the sleeve 130, the body 110 is simply moved forward within the sleeve until the tip 112 extends further beyond the sleeve 130. Conversely, the tip 112 and body 110 can be retracted into the sleeve 130 by moving the two parts 110, 130 axially with respect to one another.

In accordance with the present invention, the sleeve 130 is modified so as to have a pair of features that serve to plug or otherwise occlude and seal the otherwise opened portions of the extended incision where fluid leakage occurred in conventional design. More specifically, the sleeve 130 is defined by a body 134 and includes a first plug portion 150 and a second plug portion 160 that are configured to occupy and plug the two ends of the extended incision when the surgical instrument 100 is inserted into the incision at the tip 112 is delivered to the surgical site. It will therefore be understood that the sleeve 130 is actually received within the incision to a degree that at least the two plug portions 150, 160 are received in the incision and contact the edges of the incision.

The sleeve body 134 typically is an annular structure that has a cylindrical shape and the two plug portions 150, 160 are local protrusions that extend outwardly from the sleeve body 134 at a distal end 136 of the sleeve body 134. In order to be received in the ends of the incision or wound, when the surrounding circular sleeve body 134 is received in the incision, the two plug portions 150, 160 are typically disposed about 180 degrees from one another.

According to one embodiment, the first and second plug portions 150, 160 can generally be thought of as wing structures of the body 134 and in the illustrated embodiment, the wings 150, 160 generally represent delta wings. A delta wing is a wing whose shape when viewed from above looks like a triangle. Proximal ends 152, 162 of the wings 150, 160 do not necessarily have to be pointed as in the case of a true delta wing but instead the proximal ends 152, 162 can be more rounded so as to provide a smoother surface as opposed to a sharp point. This provides better sealing action also since the ends of the body intimately mate with the ends of the incision to produce an intimate seal between the perimeter edge of the instrument and the skin defining the incision.

During a typical small incision eye surgery, the incision 10, defined by skin edges 12, is made and then the surgical instrument 100 is delivered to the surgical site by first placing the tip 112 into the incision and then moving the surgical instrument 100 downward into the incision 10 to deliver the tip 112 to the lens nucleus in the case of cataract surgery. As the surgical instrument 100 is delivered into the incision 10, the outer circular shape of the sleeve 130 contact the edges 12 of the skin causing the edges 12 to bow out or become extended from one another. However, as the instrument 100 is pressed further into the incision, the distalmost parts of the two wing portions 150, 160 are introduced into the incision 10. Further downward movement of the instrument 100 causes a greater area of the plug portions (wings) 150, 160 to be introduced into the incision between skin edges 12. The plug portions 150, 160 thus begin to occupy more and more of what was otherwise two end openings or local leakage points of the incision. The objective is that the shape of the plug portions 150, 160 is such that the cross-sectional areas of the plug portions 150, 160 is substantially the same or closely approximates the cross-sectional areas of the respective end opening/leakage points of the incision 10, thereby resulting in an effective plugging action in these two end openings of the incision 10. In other words, the skin edges that define the incision conform to and contact the perimeter shape of the plug portions 150, 160 and the elongated body 110 and sleeve 130 such that there are substantially no gaps between the perimeter outer surface of the instrument and the skin edges. In this manner, leakage of fluid in areas around the inserted instrument is substantially eliminated, thereby forming a closed surgical site.

Each of the plug portions 150, 160 thus has dimensions, e.g., thickness, that permit it to be inserted and held within the incision between the skin edges 12 of the incision 10 when the surgical instrument 100 is inserted into the incision 10 and the tip 112 is delivered to the surgical site (lens nucleus). Since the plug portions 150, 160 generally seal against the skin edges 12 of the incision 10, the present surgical system is an at least substantially closed system in that leakage through the incision 10 (at ends thereof) is at least substantially prevented.

The sleeve 130 can be formed of a number of materials that are suitable for the intended use, including a number of different polymers. The material should have some resiliency and in particular, the wing portions 150, 160 of the sleeve body 134 should have resiliency so as to conform to the edges 12 of the incision 10 to permit a plugging action to occur. In other words, the material of the sleeve body 134 should be sufficiently malleable so that while it occludes the wound leakage, it does not restrict the movement of the cannula in and out of the eye. In one embodiment, the sleeve 130, including plug portions 150, 160 thereof, is formed of silicone.

It will be appreciated that in either embodiment, the plug portions 150, 160 actually are received within the incision 10, between the skin edges 12, as opposed to being merely placed exterior to the wound next to the skin surface. The distal tip of the instrument, partially defined by the sleeve 130, thus has a varying diameter (dimension) due to the presence and formation of the plug portions 150, 160 and in the case when the plug portions 150, 160 have delta wing shapes, the diameter progressively increases in a direction away from the distal tip.

In another aspect of the present invention and as shown best in FIGS. 4 and 6, the wing portions 150, 160 terminate in sharp proximal ends or edges 151, 161, respectively. The proximal edges 151, 161 are formed at locations where the wing portions 150, 160, respectively, are at their greatest width. The edges 151, 161 represent undercuts of the wing portions 150, 160 and in the illustrated embodiment, the edges 151, 161 are substantially perpendicular to the elongated sleeve body 134; however, this is merely one example and is not limiting of the present invention. The edges 151, 161 assist in the surgical procedure in that when the surgical instrument 100 is inserted into the incision 10, the instrument 100 extends a sufficient depth such that edges 151, 161 are received in the incision 10 and lie underneath the skin. The edges 151, 161 act as interference or stop elements in that they restrict or prevent the free removal or withdrawal of the instrument 100 from the wound 10 due to the position of the edges 151, 161 underneath the skin.

Figure 7:
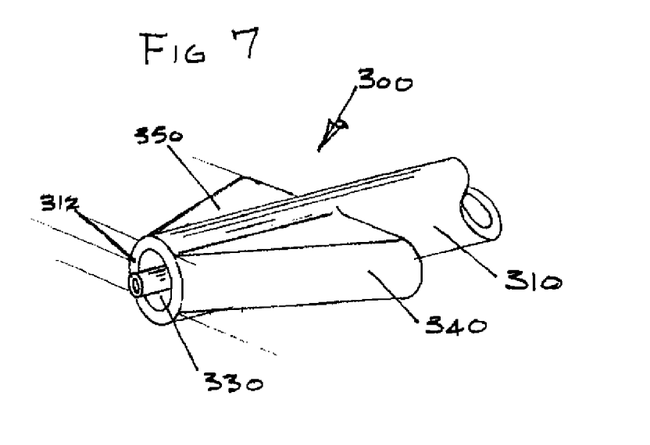
FIG. 7 is a perspective view of a surgical instrument according to a second embodiment of the present invention.

As previously mentioned, bimanual emulsification is becoming more popular in the field of small incision cataract surgery. FIG. 7 is a perspective view of an instrument 300 intended for use in bimanual procedure. As explained above, a bimanual surgical technique uses a pair of instruments inserted through two separate incisions with one of the instruments performing emulsification and aspiration of the unwanted tissue (e.g., lens nucleus), while the other instrument is provided for delivering infusion/treatment fluid to the surgical site. The instrument 300 can either be the emulsifying probe or it can be the infusion probe, with each of these instruments being inserted through its own incision in the eye to perform cataract removal surgery according to the bimanual emulsification method.

Since each of the instruments 300 is inserted into the incision 10 (FIG. 3), each would/incision experiences leakage when the conventional probe design is used. Accordingly and similar to the instrument 100 of FIG. 4, the probe 300 incorporates a plug feature at a tip portion thereof. For example, the probe 300 has an elongated body 310 that terminates in a distal tip 312 when the probe is the emulsifying probe. The elongated body 310 contains an energy means (not shown) that is operatively connected to the working tip 312 to permit the distal tip 312 which functions as a working tip to emit energy that is sufficient to break apart and emulsify the lens nucleus when the working tip 312 is placed at the surgical site. The energy means can be any of the ones mentioned above, such as ultrasound, laser, or a fluid means, such as pressurized water or water jets. The body 310 typically has a circular shape with a bore 330 extending through the body to the distal tip 312.

The bore 330 defines a passage that extends to the distalmost portion of the tip 312. The bore 330 is fluidly connected to a means for supplying a suction force to the associated passage. The means can include an outlet to which a suction pump (not shown) can be coupled. When the probe 300 is used as an infusion probe, the energy means 320 is omitted and the bore 330 carries infusion fluid to the surgical site.

In accordance with the present invention and similar to the above embodiments, the probe body 310 is modified so as to have a pair of features that serve to plug or otherwise occlude and seal the otherwise opened portions of the extended incision 10 where fluid leakage occurs. More specifically, the probe body 310 includes a first plug portion 340 and a second plug portion 350 that are configured to occupy and plug the two ends of the extended incision 10 when the probe 300 is inserted into the incision 10 at the tip 312 is delivered to the surgical site. Thus, the body 310 is actually received within the incision 10 to a degree that at least the two plug portions 340, 350 are received in the incision and contact the edges of the incision 10.

The body 310 typically is an annular structure that has a cylindrical shape and the two plug portions 340, 350 are local protrusions that extend outwardly from the body 310 at a distal end of the body 310. In order to be received in the ends of the incision or wound, when the surrounding circular body 310 is received in the incision 20, the two plug portions 340, 350 are typically disposed about 180 degrees from one another.

As with the previous embodiments, the first and second plug portions 340, 350 can generally be thought of as wing structures of the body 310, e.g., delta wings. The dimensions (width) of the plug portions 340, 350 increase, e.g., continuously, in a direction away from the distal end of the probe.

Figure 8:
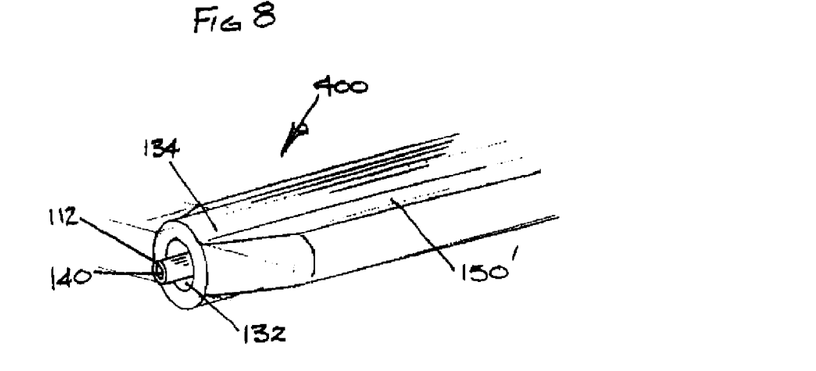
FIG. 8 is a perspective view of a surgical instrument according to a third embodiment of the present invention.
Figure 9:
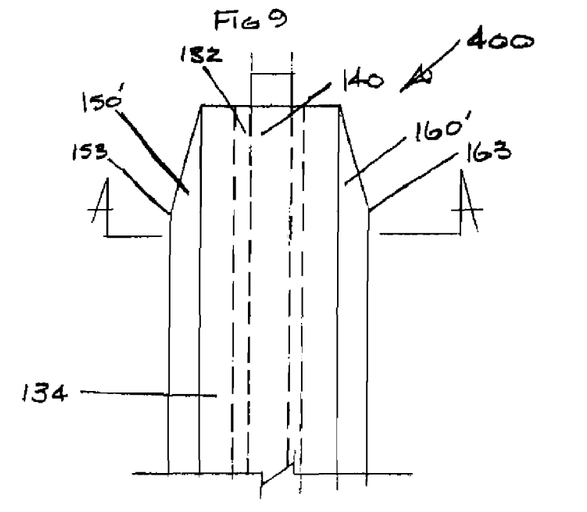
FIG. 9 is a side elevation view of the instrument of FIG. 8.
Figure 10:
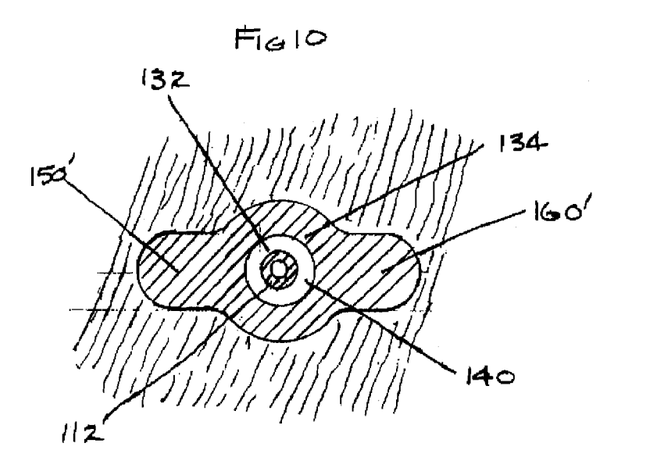
FIG. 10 is a cross-sectional view taken along the line 10-10 of FIG. 9.

Now referring to FIGS. 8-10 in which a surgical instrument 400 according to another embodiment is illustrated. The surgical instrument 400 is very similar to instrument 100 of FIG. 4 and therefore, like elements are numbered alike. In this embodiment, the instrument 400 is a coaxial type instrument like instrument 100 except that the plug portions 150', 160' do not include the undercut edges 151, 161. Instead, each of the plug portions 150', 160' tapers radially outward from the distal tip of the instrument to a point 153, 163, respectively. At these points 153, 163, the diameter (width) of the sleeve body 134 then assumes a constant diameter in a direction toward the proximal end of the instrument. When inserted into the incision, the narrowest diameter sections of the plug portions 150', 160' first contact and enter the incision and then as the instrument 400 is further inserted into the incision, the wider portions of the plug portions 150', 160' enter the incision causing a continuous filling of the open ends of the incision. Once the instrument 400 is inserted into the incision up to the points 153, 163, the previously open ends of the incision are completely occluded by the plug portions 150', 160'.

Figure 11:
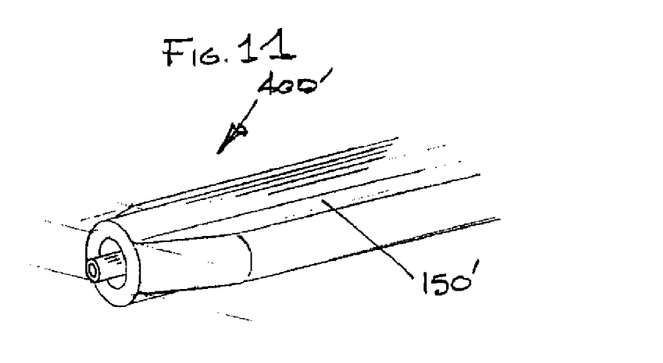
FIG. 11 is a perspective view of a surgical instrument according to a fourth embodiment of the present invention.

FIG. 11 illustrates an instrument 400' that is the bimanual instrument version of the coaxial instrument 400 shown in FIGS. 8-10. The instrument 400' can therefore be either an emulsifying probe or an infusion probe and includes the plug portions 150', 160' (FIG. 9).

Figure 12:
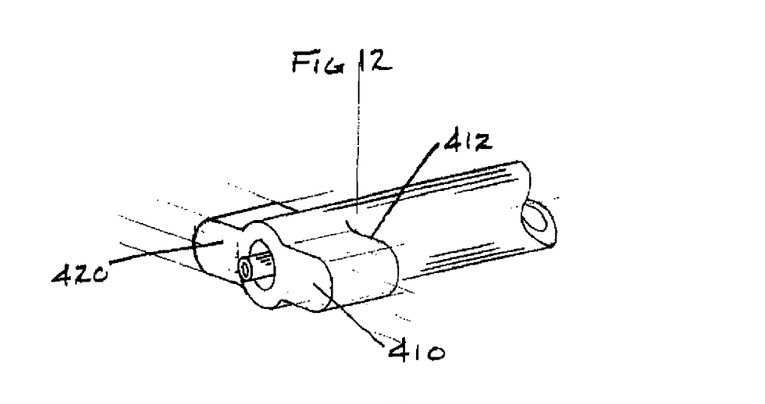
FIG. 12 is a perspective view of a surgical instrument according to a fifth embodiment of the present invention.
Figure 13:
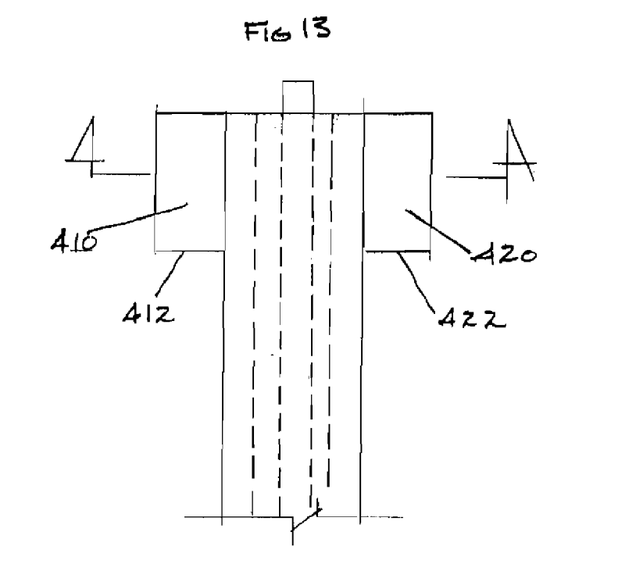
FIG. 13 is a side elevation view of the instrument of FIG. 12.
Figure 14:
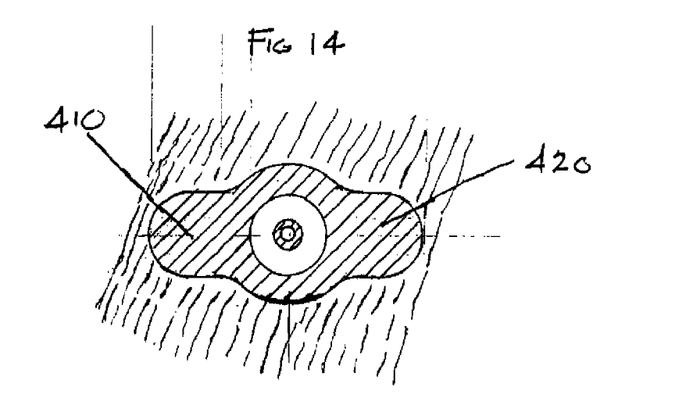
FIG. 14 is a cross-sectional view taken along the line 14-14 of FIG. 13.
Figure 15:
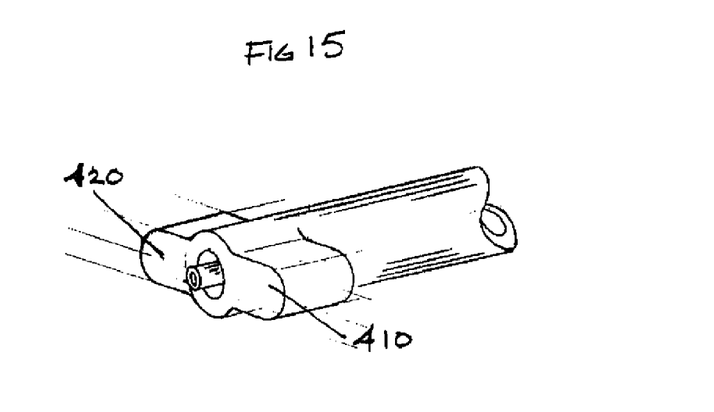
FIG. 15 is a perspective view of a surgical instrument according to a sixth embodiment of the present invention.

Instead of having a delta wing shape, the plug portions of each of the above instruments/probes and plugs can be generally in the form of two nubs 410, 420 that each has a rounded or more pointy outer edge 412, 422 as illustrated in FIGS. 12-14. In the illustrated embodiment, the nubs 410, 420 terminate in proximal undercut edges 412, 422, respectively, that are at least substantially perpendicular to the cylindrical body of the sleeve body. In this embodiment, the nubs 410, 420 have a uniform constant radial width are measured from the sleeve body from the distal end to the proximal end thereof. However, it will be appreciated, that a slight distal tapered edge can be incorporated into the nubs 410, 420 at their distal ends of the sleeve body. FIGS. 12-14 illustrate a coaxial instrument, while FIG. 15 illustrates an instrument for use in the bimanual surgical procedure.

Figure 16:
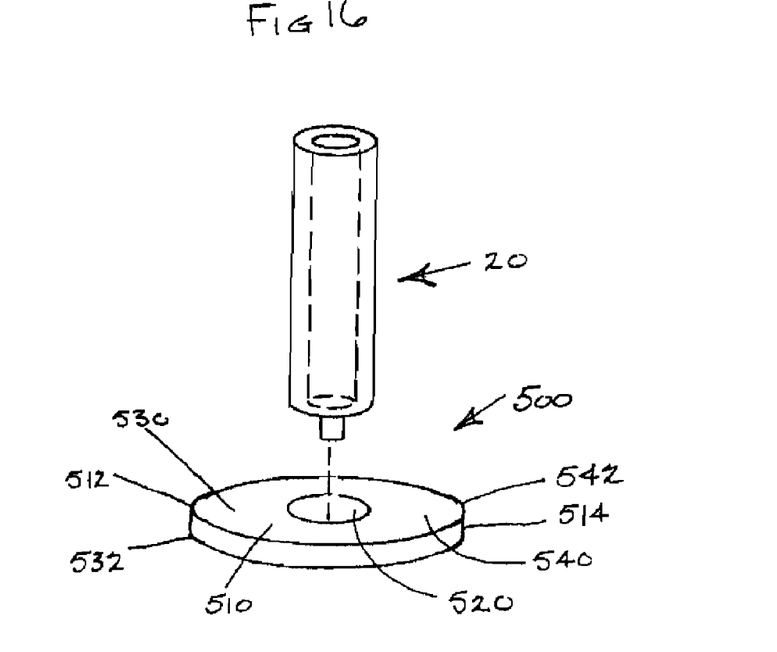
FIG. 16 is a perspective view of a plug member according to one embodiment.

In an alternative embodiment illustrated in FIG. 16, a surgical plug 500 can be provided to be used in combination with conventional coaxial or bimanual surgical instruments, generally indicated at 20, used in small incision cataract surgery. In this embodiment, the surgical plug 500 has a body 510 that includes a bore or through opening 520 that extends therethrough in a section of the body 510. Preferably, the bore 520 is centrally located in the body 510. The bore 520 has a shape that is complementary to the shape of the one or more cannulas of the surgical instrument 20 so that the surgical instrument 20 can extend through the bore 520, while at the same time, a seal is at least substantially formed between the surgical instrument 20 and the body 510 as described below. The bore 520 typically has a circular shape since most cannulas of surgical instruments have circular cross-sections. In the event that the cannula is ovoid as opposed to being circular, the bore 520 is likewise generally ovoid in shape to accommodate the cannula and to permit the cannula to slidingly travel within the bore 520 and at the same time provide a seal between the cannula's outer surface and the wall that defines the bore 220. It will be understood that the bore 220 can have other shapes that complement the shape of the cannula.

The plug body 510 has a first end 512 and a second end 514 with a first plug portion 530 being formed at the first end 512 and a second plug portion 540 being formed at the second end 514. The first and second plug portions 530, 540 can generally be thought of as contoured ends of the body 510. Distal ends 532, 542 of the portions 530, 540 are likely to be rounded so as to provide a smoother surface as opposed to a sharp point. The present construction permits the skin edges that define the incision to conform to and contact the perimeter shape of the plug body 510, including the portions 530, 540, such that there are no significant gaps between the plugt and the skin edges. In this manner, leakage of fluid in areas around the inserted plug is substantially eliminated, thereby providing a closed surgical site.

When the plug 500 is used instead of the surgical instrument 100 of the first embodiment, the plug body 510 is simply inserted into the incision 10 as by pressing the plug body 510 into the incision. The plug body 510 thus has dimensions, e.g., thickness, that permit it to be inserted and held within the incision between the skin edges 12 of the incision 10. When the plug 500 is held within the incision 10, the wider central body 510 will bow out the walls 12 of the incision 10 as the conventional cannula instruments do; however, the first and second plug portions 530, 540 serve to occupy the regions that were otherwise not occupied by the cannula and where fluid leakage occurred. As a result, fluid is at least substantially precluded from leaking at the ends of the extended incision. As soon as the plug 500 is held in position within the incision 10, the surgical instrument 20 is inserted through the bore 520 and into the incision 10. The cannula of the instrument 20 can slidingly move within the bore 520 so that the operating tip of the instrument 20 can be moved to the surgical site, such as the lens nucleus in the case of small incision cataract surgery. Once the eye surgery is completed, the surgical instrument 20 is removed from the bore 520 and then the plug 500 can be removed from the incision 10. The plug 500 can be removed with the assistance of a surgical tool, such as a tweezer like instrument or the like.

Since the plug portions 530, 540 generally seal against the skin edges of the incision and the body 510 seals against the surgical instrument 20 within the bore 520, the present surgical system is an at least substantially closed system in that leakage through the incision 10 is at least substantially prevented.

The surgical plug 500 can be formed of a number of materials that are suitable for the intended use, including a number of different polymers. The material should have some resiliency so as to form a seal with the instrument 20 as it is received in the bore 520 and moreover, the wing portions 530, 540 of the body 510 have resiliency so as to conform to the edges 12 of the incision 10 to permit a plugging action to occur. In one embodiment, the surgical plug 500 is formed of silicone.

Figure 17:
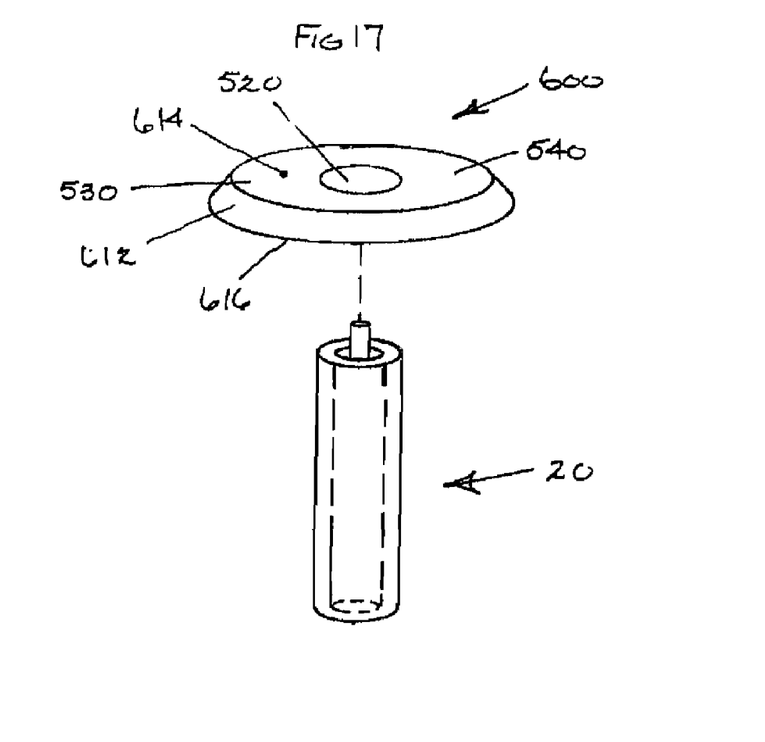
FIG. 17 is a perspective view of a plug member according to another embodiment.

FIG. 17 illustrates a plug 600 that is very similar to plug 500 of FIG. 16 with the exception that a body 610 of the plug 600 has a side edge 612 that is of a beveled construction as opposed to the straight side edge of the plug 500. In the illustrated embodiment, the side edge 612 is continuously tapered from one face 614 of the body 610 to the other opposing face 616 of the body 610. When inserting the plug 600 into the incision 10, the face 614 where the side edge 612 has its narrowest width is first inserted and then as the plug 600 is inserted more into the incision, the skin edges contact the continuously tapered (increasing width) side edge 612 toward the other face 616.

Figure 18:
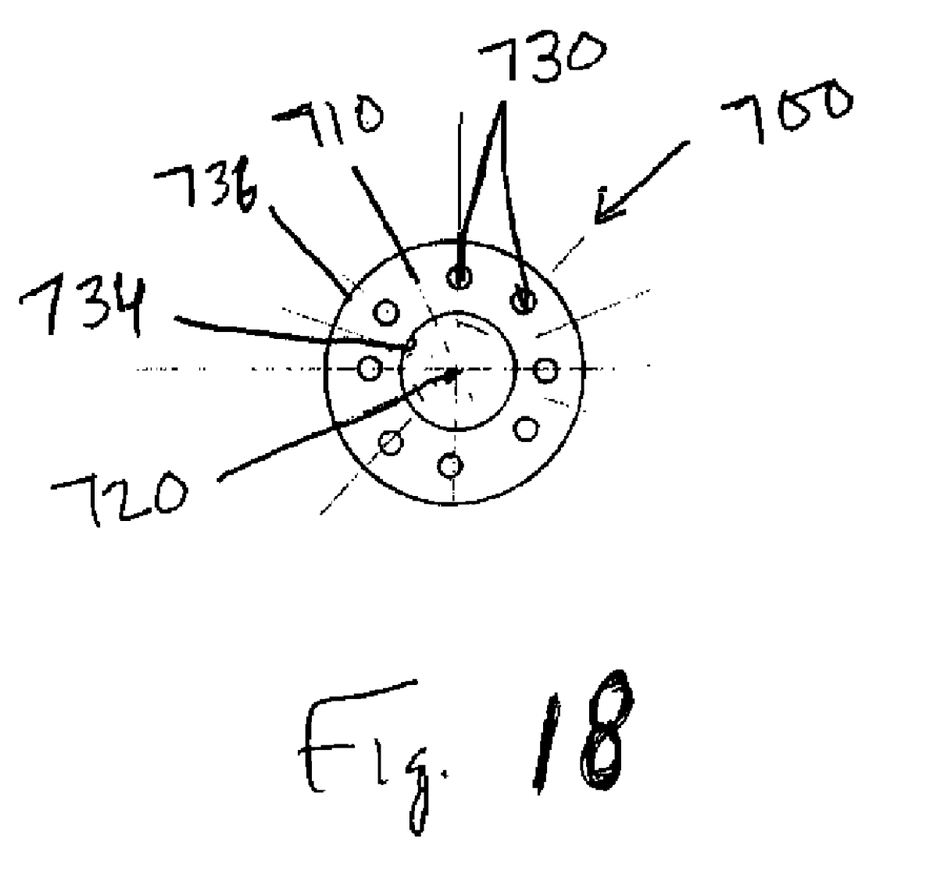
FIG. 18 is a cross-sectional view of a distal tip of an alternative surgical instrument.

In yet another embodiment, a coaxial probe 700 is illustrated in FIG. 18. The probe 700 is formed of an elongated body 710 that has a distal tip at a distal end thereof. The body 710 has an axial bore 720 formed therein and extending to the distal end. The bore 720 can have any number of cross-sectional shapes, with one shape being the illustrated circular shape. The body 710 typically has a cylindrical tubular shape with an outer diameter and an inner diameter. As with the prior embodiment, the bore 720, that defines a first fluid passage, is in fluid communication with a means for supplying a suction force to the bore 720. The means can include an outlet to which a suction pump (not shown) can be coupled.

Instead of having a separate coaxially aligned sleeve as in the earlier embodiment, the instrument 700 incorporates one or more second fluid passages 730 into the body 710 itself. As shown in the cross-sectional view of FIG. 18, the body 710 includes a plurality of second fluid passages 730 that are formed between the inner wall 734 and an outer wall 736 and are radially disposed about the bore 720. The diameter of each of the second fluid passages 730 is much less than the diameter of the bore 720. In the illustrated embodiment, there are five (5) or more second fluid passages 730 formed in the body 710 (radially about the bore 720).

Each of the second passages 730 is separate from and not in fluid communication with the bore 720 and is in fluid communication with a means for supplying fluid (treatment fluid/infusion fluid) to the second passages 730. The means can include an inlet to which a treatment fluid supply (not shown) can be coupled.

As with the instrument 100, the instrument 700 and more particularly, the body 710 thereof, is modified so as to include one of the pair of plug features disclosed herein, such as plug features 150, 160 (FIG. 4), that serve to plug or otherwise occlude the incision opening when the instrument 700 is inserted into the wound during the surgical procedure.

In addition, it will be appreciated that the plug portions of each of the above instruments/probes and plugs can be formed of the same material as the body structure from which they extend or they can be formed of a different material. For example, in the case of instrument 100 of FIG. 4, the sleeve body 134 can be formed of one material, while the plug portions 150, 160 can be formed from another material that is more resilient to permit the plug portions 150, 160 to flex and generally contact and seat against edges 12 of the incision 10.

The present invention can thus be broadly construed as a surgical instrument/tool that has a pair of discrete, local surface modifications or structures (e.g., protuberances) at a distal most portion of a working distal tip of the device. These local surface modifications are adapted to be received within the incision itself up to a predetermined depth so as to result in the incision being substantially plugged to provide an at least substantially closed surgical system where fluid leakage is greatly reduced or eliminated. A cross-sectional area of a portion of the instrument/plug that is inserted into the incision and is defined by the body of the instrument or plug and the plug portions is approximately equal to a cross-sectional area of an incision opening formed when the instrument/plug is inserted in the incision and skin edges bow open.

It will also be appreciated that in an alternative embodiment, the local surface modifications (e.g., protuberances) can be slightly spaced from the immediate distal end of the distal tip. For example, there may be a very small space at the distal end of the distal tip before the formation of the local surface modifications.

It will be understood that the present invention involves a great number of different embodiments which share a common feature that the outer body surface of the instrument that is inserted into the incision is specially contoured and configured so that it overcomes the deficiencies of the prior art and provides a structure that extends outwardly from the conventional instrument body and is shaped so as to fill the space or void created between the opposing skin edges at the ends of the incision when the instrument/plug is inserted into a central section of the incision. Preferably, the two opposing skin edges seat against or seal against the outer surface of the instrument, including the plug portions, and to facilitate this the instrument is preferably formed of a pliable material that permits movement or flexing of the instrument as it is inserted into the incision and forces the skin edges to separate.

While the surgical instruments described herein as having particular utility in eye surgery and particularly, for cataract removal, it will be understood that the present surgical instruments and plugs can be embodied and used in a number of different applications. In other words, the surgical instruments and plugs can be easily adapted for other surgical purposes besides the ones described herein.

Figure 19:
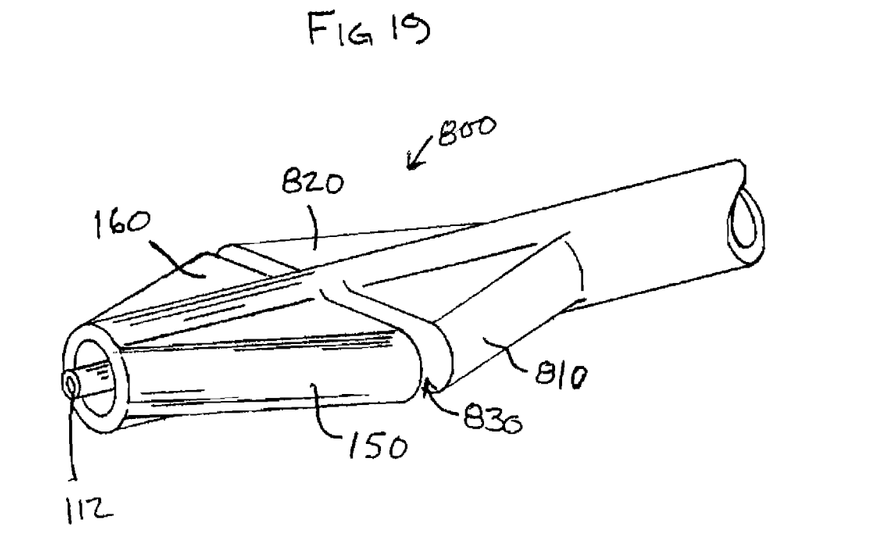
FIG. 19 is a perspective view of a surgical instrument according to yet another embodiment of the present invention.
Figure 20:
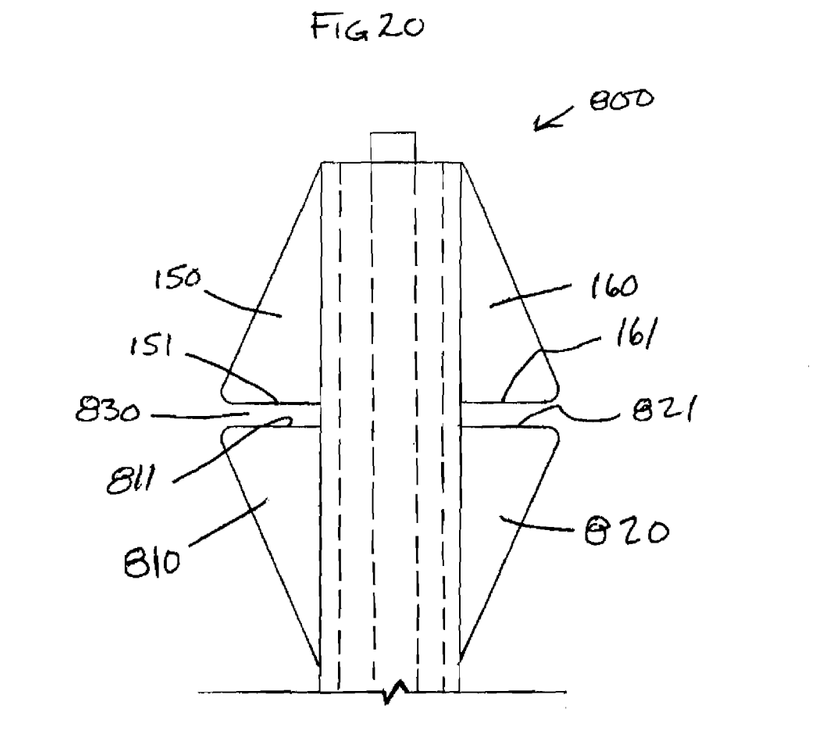
FIG. 20 is a cross-sectional view of the instrument of FIG. 19.

FIGS. 19-20 illustrate another embodiment of the present invention which is similar to the embodiment shown in FIGS. 4-6 with the exception that instrument 800 includes two sets of plugs in the form of the plugs 150, 160, as previously described with reference to FIGS. 4-6 and another set of spaced plugs 810, 820. As illustrated, the plugs 810, 820 are preferably mirror images of the plugs 150, 160, respectively, with a space 830 being formed therebetween. The space 830 can be thought of as a radial or circumferential band that extends around the sleeve of the instrument.

The plugs 810, 820 take the form of wing portions that terminate in sharp distal ends or edges 811, 821, respectively (that are opposite and spaced apart from edges 151, 161, respectively). The distal edges 811, 821 are formed at locations where the wing portions 810, 820, respectively, are at their greatest width. The edges 811, 821 are substantially perpendicular to the elongated sleeve body 134; however, this is merely one example and is not limiting of the present invention. The edges 811, 821, in combination with edges 151, 161 assist in the surgical procedure in that when the surgical instrument 800 is inserted into the incision 10, the instrument 800 extends a sufficient depth such that edges 151, 161 are received in the incision 10 and lie underneath the skin, while the skin is received into the annular space 830. The edges 151, 161 act as interference or stop elements in that they restrict or prevent the free removal or withdrawal of the instrument 800 from the wound 10 due to the position of the edges 151, 161 underneath the skin. Similarly, the edges 811, 821 act as interference or stop element in that they restrict or prevent the instrument 800 from being inserted too deep into the wound. In other words, the space 830 is dimensioned to receive the skin after the edges 151, 161 clear and seat underneath the skin (inner skin surface) and therefore, this results in the edges 811, 821 seating against the outer surface of the skin. Since the edges 811, 821 have greater dimensions then the incision, the degree of travel of the instrument in a direction toward the skin and into the body is limited. In this manner, the plugs 810, 820 act as stops in a direction opposite the direction in which the plugs 150, 160 act as stops.

It will also be understood that while the use of two sets of spaced plugs 150, 160, 810, and 820 is particularly suited for bimanual emulsification, it is not limited to this type of instrument but can be used in other application, including the above described coaxial system which is actually shown in FIGS. 19 and 20.

Figure 21:
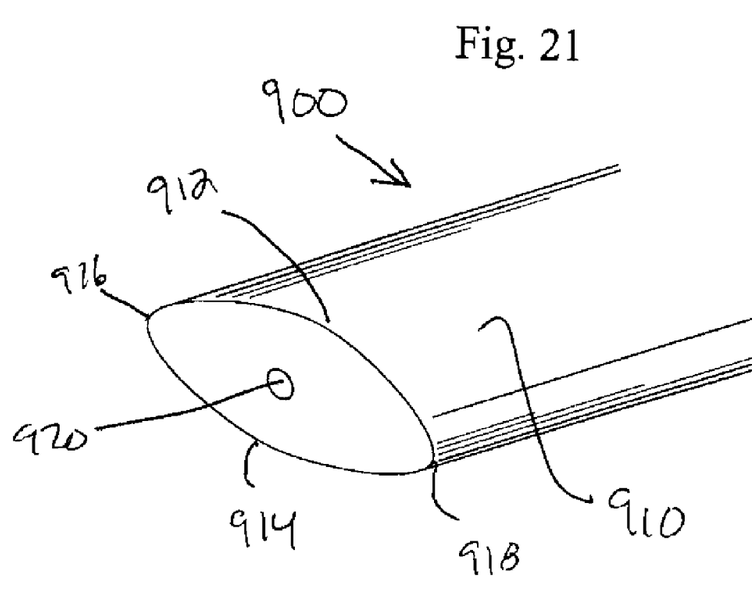
FIG. 21 is a perspective view of a surgical instrument according to yet another embodiment of the present invention.
Figure 22:
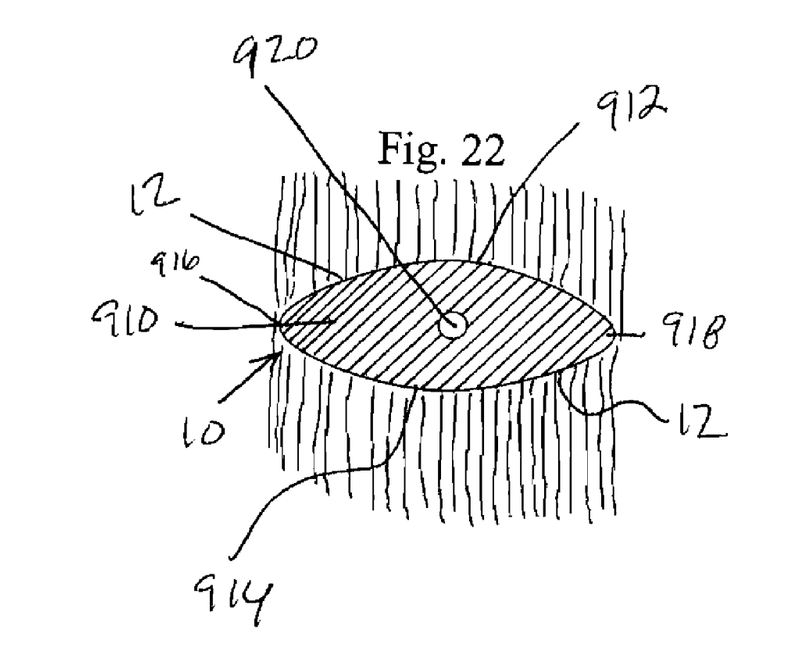
FIG. 22 is a cross-sectional view of the surgical instrument of FIG. 21.

FIGS. 21 and 22 illustrate a surgical instrument 900 according to yet another embodiment of the present invention. The surgical instrument 900 can be any number of different types of instruments that are intended to be inserted into incision 10, which is defined by skin edges 12. For example, the surgical instrument 900 can be in the form of a cannula or the like or some other type of instrument that is designed to deliver a fluid to the surgical site and/or remove fluid and/or material from the surgical site as by aspiration or some other means.

Conventional cannulas has round bodies and therefore suffer from the same problems discussed with reference to FIGS. 1-3. The surgical instrument 900 is constructed so that it has an elongated body 910 that is shaped so that when the surgical instrument 900 is inserted into the incision 10, skin edges 12 bow out but remain in a substantially sealed relationship with the outer surface of the body 910, thereby resulting in a complete filling of the incision 10 and no open ends as is the case with a round cannula, see FIGS. 1-3. The body 910 thus has a cross-sectional shape generally in the form of an "eye" or in other words, the body 910 is generally ovoid in shape and preferably has slightly curved or rounded ends and opposed to sharp pointy ends. The body 910 thus has a general appearance of a football or similar generally ovoid object but in any event, the shape of the body 910 complements the natural tendency for the skin edges 12 to bow out as an object is inserted into the incision. Thus, the body 910 has one or more and preferably two opposing convex surfaces 912, 914 that seat against the skin edges 12 that define the incision 10. The interface between each convex surface 912, 914 and the adjacent skin edge 12 is one of sealed character such that fluid is at least substantially prevented from flowing between the sides of the body 910 and the skin edges 12. In addition, the ends 916, 918 of the body 910 likewise at least substantially form a seal with the respective ends of the incision 10.

The body 910 has a lumen 920 formed longitudinally therethrough from one end to the other end. The lumen 920 is located generally in the center of the body 910; however, it can be formed in any location. The lumen 920 is intended to either carry a fluid to the surgical site and/or remove a fluid and/or material from the surgical site. As with the other previously described embodiments of the present invention, the instrument 900 overcomes the deficiencies associated with the prior art, e.g., FIGS. 1-3.

Figure 23:
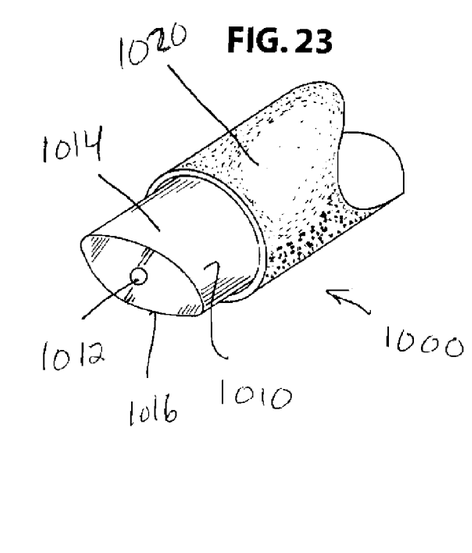
FIG. 23 is a perspective view of a surgical instrument according to another embodiment of the present invention.
Figure 24:
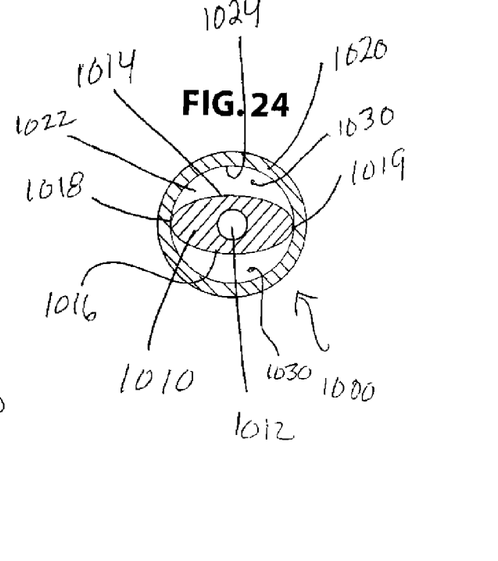
FIG. 24 is a cross-sectional view of the surgical instrument of FIG. 23.

Referring now to FIGS. 23-24, another embodiment of the present invention is illustrated. FIGS. 1-2 illustrate a conventional Phaco type needle that is used to perform a surgical operation. The Phaco needle is formed of a solid, metal needle structure and a softer sleeve (silicone material) that surrounds the needle structure. The sleeve is adjustable about the length of the needle as by sliding the sleeve over a length of the needle. In the conventional design, the innermost solid needle has a circular shape and the sleeve has a circular shape as well.

In the embodiment of FIGS. 23-24, a conventional Phaco type needle is modified according to the principles of the present invention as set forth above with respect to other embodiments. More specifically, a surgical instrument 1000, in the form of a Phaco type needle, is illustrated and includes a needle or cannula 1010 that has a bore 1012 extending therethrough for either delivering and/or aspirating a fluid or a material or combination thereof. The needle 1010 is a solid structure that is formed from a rigid material, such as a metal, and in accordance with one embodiment, the needle 1010 has a generally ovoid shape in that it is defined by two convex surfaces 1014, 1016 that converge and meet (intersect) at their two ends 1018, 1019. These ends 1018, 1019 define two sides of the needle 1010. In other words, the needle 1010 has a "football" like shape or it can also be described as being an ellipsoid or a prolate spheroid which means that its axis of symmetry is longer than its other axes.

The instrument 1000 also includes a sleeve 1020 that surrounds the needle 1010 and in one embodiment, the sleeve 1020 can be in the form of a traditional Phako sleeve that has a circular shape. It will be appreciated that since the sleeve 1020 is formed of a resilient, pliable material, such as silicone, the sleeve 1020 can flex when the needle 1020 is inserted into a hollow space 1022 of the sleeve 1020. The sleeve 1020 is thus a hollow structure with space 1022 being centrally located. When the ovoid shaped needle 1010 is inserted into the space 1022, the sides 1018, 1019 of the needle 1010 contact an inner surface 1024 of the sleeve 1020 and locally deform the sleeve 1020. For example, the insertion of the ovoid shaped needle 1010 into the space 1022 causes the sleeve 1020 to lose its circular shape and instead two local areas of the sleeve 1020 become stretched outwardly causing a shift in the shape of the sleeve 1020 more towards an ovoid shape or ellipsoid shaped or a prolate spheroid shape due to the sides 1018, 1019 contacting the inner surface 1024 in two opposing locations.

Since the needle 1010 and the sleeve 1020 do not each have a circular shape, the instrument 1000 does not have an annular space formed between the needle and the sleeve as is the case with the conventional Phako Needle of FIGS. 1 and 2. Instead a pair of crescent shaped passages or channels 1030 are formed between the needle 1010 and the sleeve 1020. As with the other embodiments, these passages or channels 1030 are designed to carry a fluid and/or material or a combination thereto to and/or from the surgical site. For example, irrigation fluid can be delivered through the crescent shaped channels 1030 to the surgical site and fluid and/or material (e.g., fluid and tissue) can be removed (aspirated) from the surgical site through the needle bore 1012.

The crescent shaped channels 1030 are formed opposite one another and it will also be appreciated that the size (area) of the channels 1030 depends on the radius of curvature of the outer convex surfaces 1014, 1016 of the needle and the radius of curvature of the inner surface 1024 of the sleeve 1020. For example, as the ratio between the curvature of inner surface 1024 and the curvature of the outer surface 1014, 1016 increases, the area of the channels 1030 increases. Conversely, as the ratio decreases, the area of channels 1030 decreases.

Figure 25:
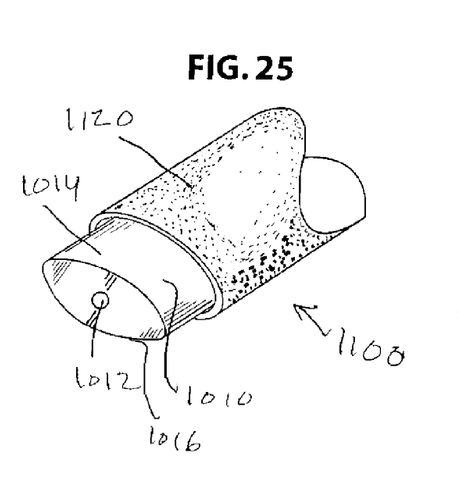
FIG. 25 is a perspective view of a surgical instrument according to yet another embodiment of the present invention.
Figure 26:
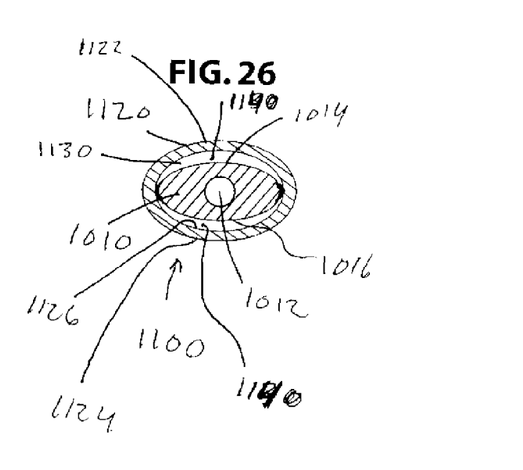
FIG. 26 is a cross-sectional view of the surgical instrument of FIG. 25.

Now referring to FIGS. 25-26, in which yet another embodiment of the present invention is illustrated. In this embodiment, a surgical instrument 1100 is similar to the instrument 1000 in that it contains ovoid shaped needle 1010; however, instead of containing sleeve 1020 which has a circular shape in a normal condition, a sleeve 1120 is provided and like the needle 1010, the sleeve 1120 has an ovoid shape as shown in FIGS. 25-26. In other words, in its relaxed state, the sleeve 1120 has a pair of opposing convex shaped outer surfaces 1122, 1124 and an inner bore, space, cavity 1130 of the sleeve 1120 is not circular but it ovoid in shape. The shape of the cavity 1130 is thus complementary to the shape of the needle 1010; however, since a space between the needle 1010 and the sleeve 1120 is necessary for delivery and/or removal of fluid and/or material, the radiuses of curvature of an inner surface 1126 of the sleeve 1120 and of the outer surface 1122, 1124 is selected such that a pair of passages or channels 1140 are formed. As with the embodiment of FIGS. 23-24, the passages or channels 1140 can take a crescent shape and the area of the channels 1140 increases as the ratio between the curvature of inner surface 1126 and the curvature of the outer surface 1122, 1124 increases. Conversely, as the ratio decreases, the area of channels 1140 decreases.

As with the other prior embodiments, the insertion of either instrument 1000 or 1100 into an incision results in a plugging of the incision (a continuous filling of the open ends of the incision).

Having described embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A surgical instrument for insertion in an incision during surgical treatment and removal of tissue comprising:
an inner elongated needle having an ovoid shape and a bore extending therethrough; and
a deformable hollow outer sleeve that is separate from the needle and surrounds the ovoid shaped needle such that two side regions of the needle continuously contact an inner surface of the sleeve at two opposite locations both in a rest, non-deformed position prior to insertion of the instrument in the incision and post insertion so as to define a pair of fluid channels that are located between convex outer surfaces of the needle and the inner surface of the sleeve, the hollow sleeve being an outermost member of the surgical instrument for contacting skin edges that define the incision and wherein the inner elongated needle and the hollow sleeve are each independently movable relative to one another.

2. The surgical instrument of claim 1, wherein the needle is defined by a pair of convex outer surfaces that converge at their ends to define the two side regions of the needle.

3. The surgical instrument of claim 1, wherein the needle is formed of a rigid material and the sleeve is formed of a flexible material that permits the sleeve to be slid over the needle.

4. The surgical instrument of claim 3, wherein the needle is formed of a metal and the sleeve is formed of silicone.

5. The surgical instrument of claim 1, wherein the sleeve has a circular shape in its relaxed state and upon insertion of the needle, the sleeve deforms to a shape other than a circle.

6. The surgical instrument of claim 1, wherein each of the pair of channels has a crescent shape.

7. The surgical instrument of claim 1, wherein the pair of channels are fluidly separated from one another at the two locations where the two side regions of needle are in contact and engaged with the inner surface of the sleeve.

8. The surgical instrument of claim 1, wherein an area of each of the channels is substantially equal.

9. The surgical instrument of claim 1, wherein the shape of the sleeve, when deformed by insertion of the needle, is configured to be received within the incision during the surgical treatment and removal of the tissue so as to plug opposite ends of the incision and provide an at least substantially closed surgical site.

10. A surgical instrument for insertion in an incision during surgical treatment and removal of tissue comprising:
an inner elongated needle having an ovoid shape and a bore extending therethrough; and
a hollow outer sleeve that is separate from the needle and surrounds the ovoid shaped needle such that two side regions of the needle continuously contact an inner surface of the sleeve at two opposite locations so as to define a pair of separate fluid channels that are located between convex outer surfaces of the needle and the inner surface of the sleeve, wherein in a relaxed condition prior to insertion of the needle, the sleeve has an ovoid shape and is in contact with the needle at the two locations and the pair of separate fluid channels is defined by the points of contact between the needle and the sleeve, the hollow sleeve being an outermost member of the surgical instrument for contacting skin edges that define the incision and wherein the inner elongated needle and the hollow sleeve are each independently movable relative to one another.

11. The surgical instrument of claim 10, wherein the needle is defined by a pair of convex outer surfaces that converge at their ends to define the two side regions of the needle.

12. The surgical instrument of claim 10, wherein the needle is formed of a rigid material and the sleeve is formed of a flexible material that permits the sleeve to be slid over the needle.

13. The surgical instrument of claim 12, wherein the needle is formed of a metal and the sleeve is formed of silicone.

14. The surgical instrument of claim 10, wherein each of the pair of channels has a crescent shape.

15. The surgical instrument of claim 10, wherein the pair of channels are fluidly separated from one another at the two locations where the two side regions of needle are in contact and engaged with the inner surface of the sleeve.

16. The surgical instrument of claim 10, wherein an area of each of the channels is substantially equal.

17. The surgical instrument of claim 10, wherein the ovoid shape of the sleeve is configured to be received within the incision during the surgical treatment and removal of the tissue so as to plug opposite ends of the incision and provide an at least substantially closed surgical site.

* * * * *